United States Patent
Otsubo et al.

(10) Patent No.: US 7,169,136 B2
(45) Date of Patent: Jan. 30, 2007

(54) PULL-ON DISPOSABLE DIAPER

(75) Inventors: Toshifumi Otsubo, Kagawa-ken (JP); Shunsuke Takino, Kagawa-ken (JP)

(73) Assignee: Uni-Charm Co., Ltd., Ehime-ken (JP)

( * ) Notice: Subject to any disclaimer, the term of this patent is extended or adjusted under 35 U.S.C. 154(b) by 0 days.

(21) Appl. No.: 10/924,256

(22) Filed: Aug. 24, 2004

(65) Prior Publication Data
US 2005/0288648 A1 Dec. 29, 2005

Related U.S. Application Data

(63) Continuation of application No. PCT/JP03/01804, filed on Feb. 19, 2003.

(30) Foreign Application Priority Data

Mar. 13, 2002 (JP) .............................. 2002-069028

(51) Int. Cl.
*A61F 13/20* (2006.01)

(52) U.S. Cl. .................. 604/385.21; 604/385.201; 604/385.22

(58) Field of Classification Search ............................. 604/385.01–385.201, 385.28, 380, 385.22–385.31, 604/358
See application file for complete search history.

(56) References Cited

U.S. PATENT DOCUMENTS

| | | | | |
|---|---|---|---|---|
| 3,196,874 A * | 7/1965 | Hrubecky | .................... | 604/366 |
| 3,710,797 A * | 1/1973 | Marsan | ................. | 604/385.201 |
| 3,724,464 A * | 4/1973 | Enloe | .......................... | 604/365 |
| 3,774,610 A * | 11/1973 | Eckert et al. | ................ | 604/365 |
| 3,848,595 A * | 11/1974 | Endres | ................. | 604/385.201 |
| 3,860,004 A * | 1/1975 | Nystrand | ..................... | 604/365 |
| 3,924,627 A * | 12/1975 | Nystrand | ..................... | 604/365 |
| 3,968,799 A * | 7/1976 | Schrading | .................... | 604/365 |
| 4,067,336 A * | 1/1978 | Johnson | ....................... | 604/389 |
| 4,675,012 A * | 6/1987 | Rooyakkers | ................. | 604/349 |
| 4,772,280 A * | 9/1988 | Rooyakkers | ................. | 604/349 |
| 4,946,454 A * | 8/1990 | Schmidt | ................. | 604/385.19 |
| 5,746,730 A * | 5/1998 | Suzuki et al. | ........... | 604/385.26 |
| 6,102,892 A * | 8/2000 | Putzer et al. | ........... | 604/385.01 |
| 6,666,851 B2 * | 12/2003 | Otsubo et al. | ......... | 604/385.201 |
| 2002/0068919 A1* | 6/2002 | Shinohara et al. | ...... | 604/385.27 |

(Continued)

FOREIGN PATENT DOCUMENTS

JP 50-21845 3/1975

(Continued)

*Primary Examiner*—Tatyana Zalukaeva
*Assistant Examiner*—Ginger Chapman
(74) *Attorney, Agent, or Firm*—Lowe Hauptman & Berner, LLP

(57) ABSTRACT

A pull-on disposable diaper is composed of a front waist region, a rear waist region, a crotch region extending between these waist regions and a body fluid absorbing component formed on an inner side of these regions. The absorbing component is formed in the crotch region with a V-shaped first folding guide, a V-shaped second folding guide and a third folding guide extending in a transverse direction between the first and second folding guides. The absorbing component is folded along the third folding guide so that a core forming a part of the component may have its outer surface sections facing each other and along the first and second folding guides so that the core may have its inner surface sections facing each other.

6 Claims, 14 Drawing Sheets

U.S. PATENT DOCUMENTS

| | | | |
|---|---|---|---|
| 2005/0004545 A1* | 1/2005 | Shimada et al. | 604/385.01 |
| 2005/0038404 A1* | 2/2005 | Takino et al. | 604/385.27 |
| 2005/0131375 A1* | 6/2005 | Sasaki et al. | 604/385.28 |
| 2005/0143711 A1* | 6/2005 | Otsubo et al. | 604/396 |
| 2005/0148989 A1* | 7/2005 | Otsubo et al. | 604/396 |

FOREIGN PATENT DOCUMENTS

| | | |
|---|---|---|
| JP | 50-33044 | 3/1975 |
| JP | 2002-035033 | 2/2002 |
| JP | 2003-010244 | 1/2003 |

* cited by examiner

PULL-ON DISPOSABLE DIAPER

This application is a continuation of International Application No. PCT/JP03/01804 filed Feb. 19, 2003, which claims priority to Japanese Application No. 2002-069028 filed Mar. 13, 2002, all of which are hereby incorporated by reference herein in their entirety.

TECHNICAL FIELD OF THE INVENTION

This invention relates to a pull-on disposable diaper.

Background Art of the Invention

Japanese Patent Application No. 1975-33044A discloses a foldup-type disposable diaper 201 as shown in FIG. 15 of the accompanying drawings. This diaper 201 is composed of a liquid-absorbent pad, a liquid-pervious inner sheet 222 and a liquid-impervious outer sheet 223 so as to present a rectangle and this rectangle is then folded along a transversal 210a orthogonal to long sides of the rectangle in two halves in a longitudinal direction. Simultaneously, the diaper is tucked inwardly so that transversely opposite edges on the transversal 210a may face each at a middle point of the transversal 210a so as to form pockets 218. In the case of this diaper, surface sections of the sheet 223 facing each other as the diaper is tucked inwardly in this manner are partially bonded to each other in order to prevent the respective pockets 218 from getting out of initial shapes thereof even after the diaper has been developed to put the diaper on a wearer's body. The diaper arranged in such a manner is effective to prevent bodily discharges from leaking regardless of its rectangular shape because a region of the diaper destined to cover the wearer's crotch is sufficiently narrow to be fit closely against the wearer's crotch.

Japanese Utility Model Application No. 1972-36734A discloses a foldup-type diaper made from a rectangular strip. In the case of this diaper also, the diaper is tucked inwardly from its transversely opposite edges in a longitudinally middle zone of the diaper. The crotch region of the diaper obtained in this manner has its width sufficiently reduced to be fit closely against the wearer's crotch and thereby to alleviate an anxiety of sideways urine leakage.

Both of the above-cited conventional diapers are of the rectangular open-type and adapted to be put on an infant's body by flatly developing the diaper and applying it to the hip of the infant lying on his or her back. However, it is likely that the regions of the diaper having previously been folded and tucked might get out of initial shapes thereof as the diaper is flattened and the function of these regions might be insufficient after the diaper has been put on the wearer's body. The diaper disclosed by Japanese Patent Application No. 1975-33044A intends to prevent the diaper from getting out of its initial shape by partially bonding together the surface sections opposed to each other as the diaper is folded and tucked. However, such a bonding may obstruct the diaper to be flatly developed and retard operation of putting the diaper on the wearer's body. In both of the above-cited conventional diapers, the width of the region destined to cover the wearer's crotch is relatively narrow. Should bodily discharges are not received by this region, bodily discharges may leak out of the diaper and contaminate the wearer's clothes and/or body.

DISCLOSURE OF THE INVENTION

It is an object of this invention to provide a pull-on disposable diaper improved so that the problems accompanying the conventional diaper as have been described above may be effectively eliminated.

According to this invention, there is provided a pull-on disposable diaper having a height direction and a transverse direction being orthogonal to the height direction. The diaper is generally symmetric about a center line bisecting the diaper in the transverse direction. The diaper comprises a pants-like covering component having an inner surface facing a wearer's body and an outer surface facing a wearer's garment. The covering component is composed of a front waist region, a rear waist region and a crotch region adapted to cover a wearer's front region, a wearer's rear region and a wearer's crotch region, respectively. The covering component has a waist-hole and a pair of leg-holes, and is provided with an absorbing component lying on the inner surface and extending over the crotch region into the front and rear waist regions.

This invention further comprises that the absorbing component having a liquid-absorbent core and a liquid-pervious cover sheet. The core has a generally rectangular shape and has an inner surface and an outer surface. The cover sheet covers at least the inner surface of the inner and outer surfaces of the core. The absorbing component formed in the crotch region is provided with a first folding guide extending from a middle zone between transversely opposite side edges which extend, in turn, parallel to each other in the height direction to the respective side edges so as to veer toward the front waist region, a second folding guide extending in the similar manner to the respective side edges so as to veer toward the rear waist region and a third folding guide extending in a transverse direction between the first and second folding guides. The absorbing component is folded on both sides of the center line along the third folding guide so that the core may have its outer surface sections facing to each other and along the first and second folding guides so that the core may have its inner surface sections facing to each other.

This invention includes the following embodiments.

At least the first and second folding guides of the first–third folding guides serve as V-shaped folding guides having a relatively low stiffness which are formed in the absorbing component.

At least the first and second folding guides of the first–third folding guides serve as V-shaped folding guides having a relatively high stiffness which are formed in the absorbing component.

The crotch region is provided on the outer surface of the absorbing component with flaps extending outward of the absorbing component in the transverse direction and defining peripheral edges of the respective leg-holes. The flaps are elastically stretchable in a circumferential direction of the leg-holes, the outer surface of the absorbing component is separated from the flaps at least along the side edges and in vicinities of the side edges and the zones separated from the flaps are covered with the cover sheet.

The crotch region includes a liquid-impervious sheet. The cover sheet is folded back so as to wrap not only the inner surface of the core but also the outer surface of the core along of the side edges, and the core is also capable, in vicinities of the side edges, of absorbing the amount of bodily discharges present between the cover sheet and the liquid-impervious sheet from the outer surface through the cover sheet.

The outer surface of the core is covered in its transversely middle zone with a liquid-impervious sheet.

The diaper has at least the cover sheet on the outer surface of the core, a breathable nonwoven fabric sheet on an outer surface of the cover sheet, and a plastic film on an outer surface of the nonwoven fabric sheet as the liquid-impervious sheet.

DESCRIPTION OF THE BEST MODE FOR WORKING OF THE INVENTION

Details of a pull-on disposable diaper will be more fully understood from the description given hereunder in reference to the accompanying drawings.

Figure 1:
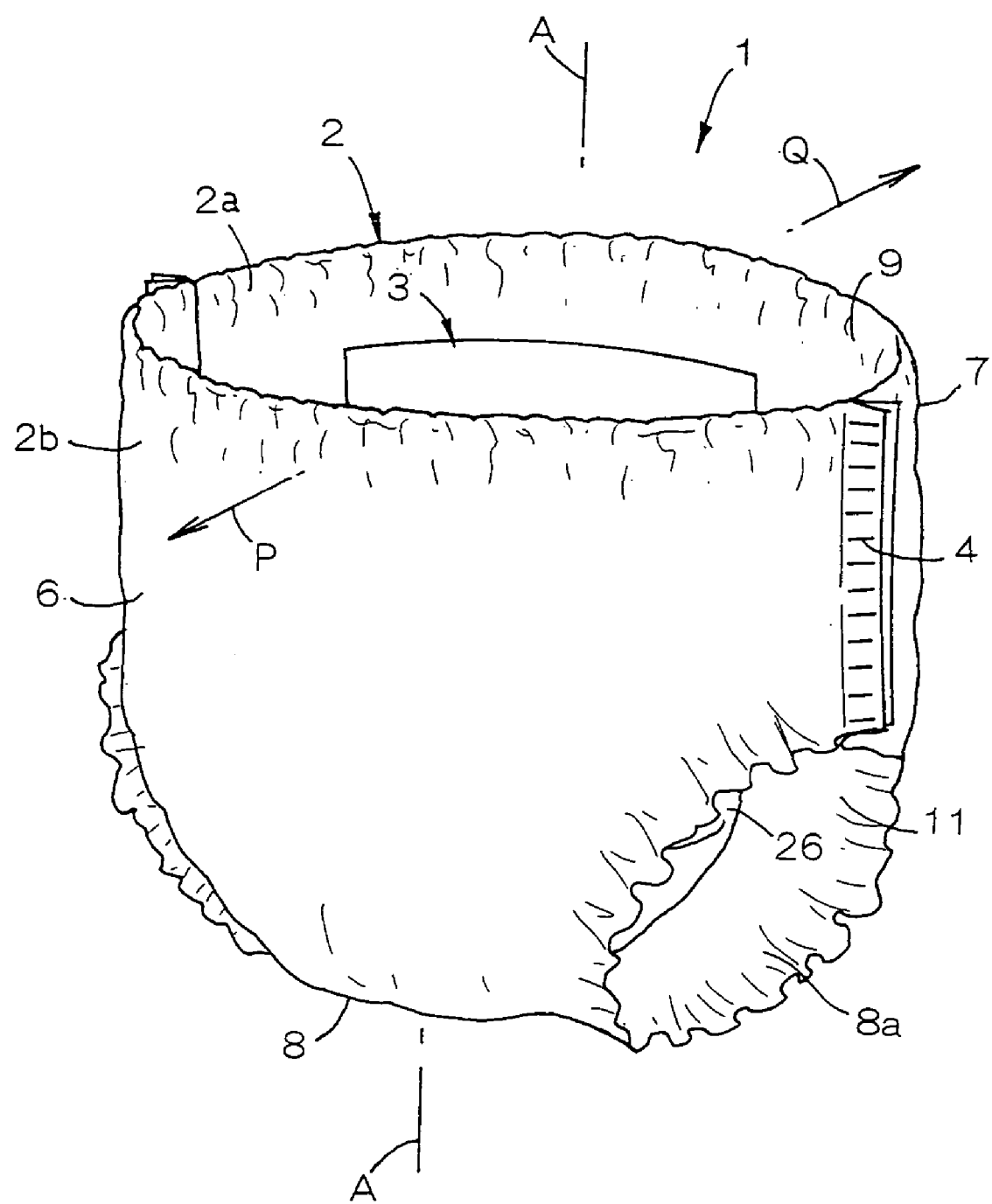
FIG. 1 is a perspective view showing a pull-on disposable diaper according to this invention.
Figure 2:
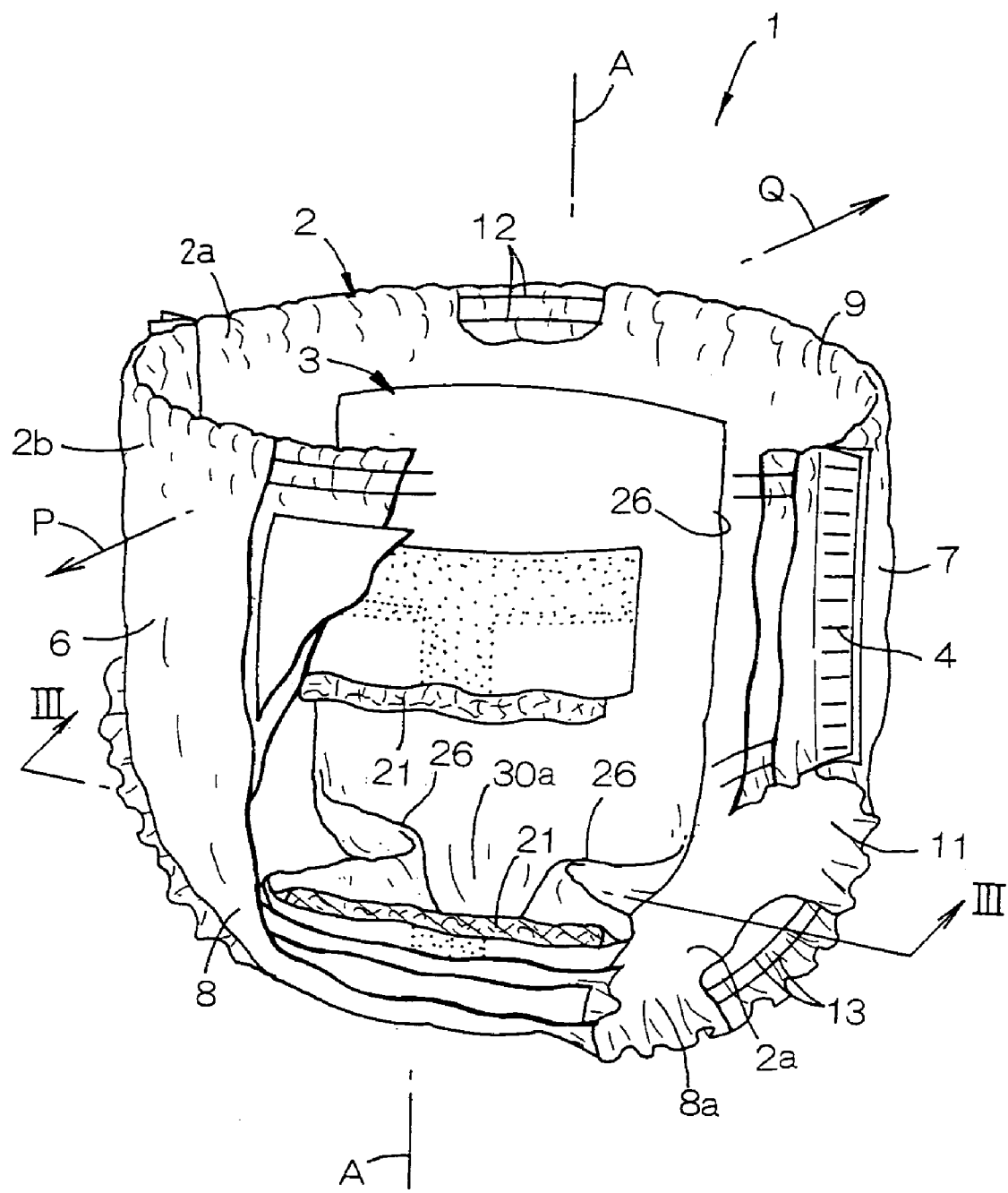
FIG. 2 is a partially cutaway perspective view showing the diaper of FIG. 1.
Figure 3:
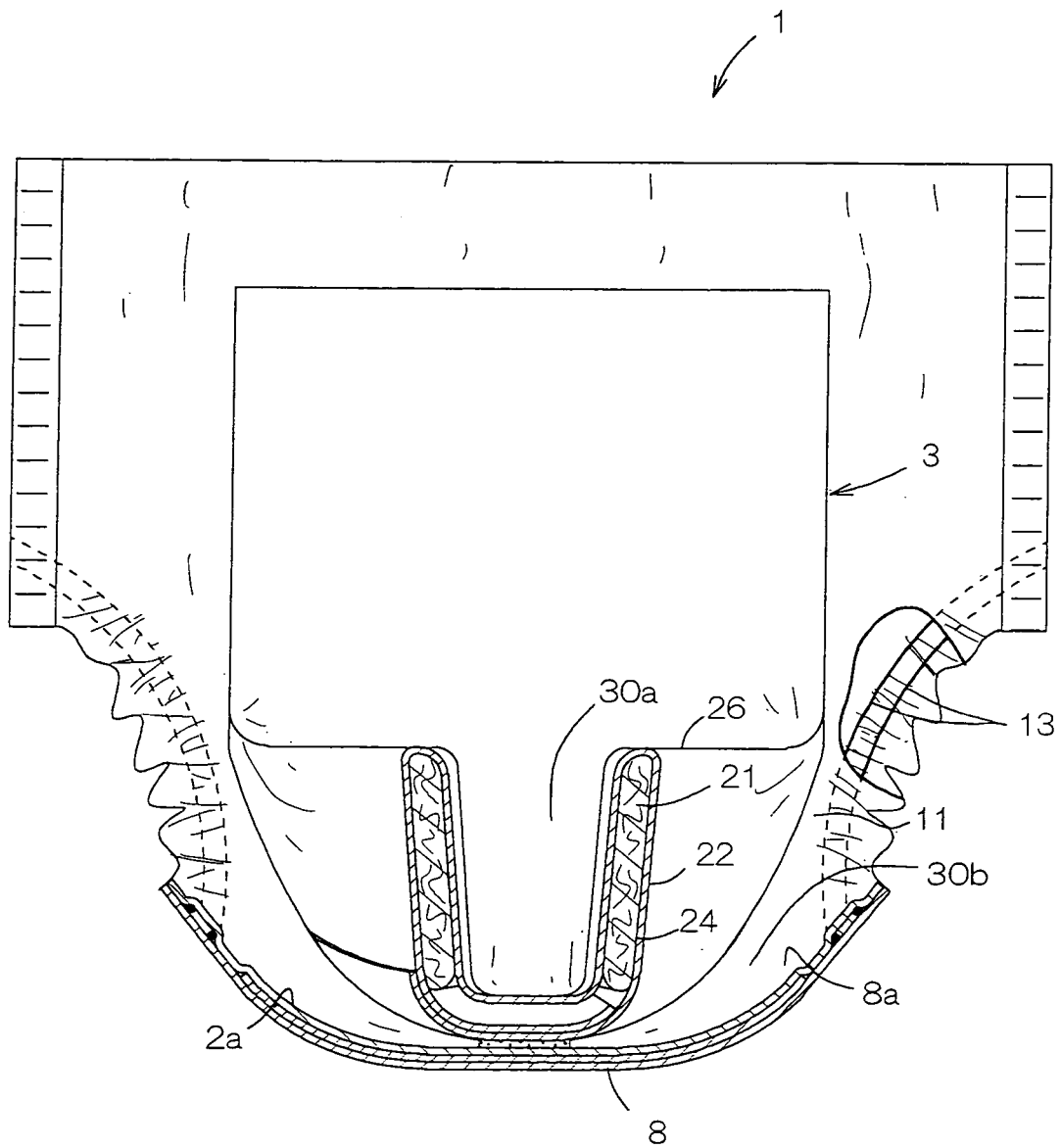
FIG. 3 is a sectional view taken along a line III—III in FIG. 2.

FIG. 1 is a perspective view showing a pull-on disposable diaper 1 according to this invention, FIG. 2 is a partially cut away perspective view showing the diaper 1 of FIG. 1 and FIG. 3 is a sectional view taken along a line III—III in FIG. 2. The diaper 1 has a height direction corresponding to a vertical direction in FIGS. 1, 2 and 3, a transverse direction and a back-and-forth direction. The diaper 1 basically comprises a pants-like covering component 2 and an absorbing component 3 functioning to contain bodily discharges. The covering component 2 has an inner surface 2a facing a wearer's body and an outer surface 2b facing wearer's clothes. This covering component 2 is composed of a front waist region 6, a rear waist region 7 and a crotch region 8 adapted to cover wearer's front, rear and crotch regions, respectively. The front and rear waist regions 6, 7 are overlaid together along transversely opposite side edge portions and joined at zones 4 arranged intermittently in a vertical direction along these opposite side edge portions so that the front waist region 6, the rear waist region 7 and the crotch region 8 cooperate one with another to define a waist-hole 9 and a pair of leg-holes 11. The waist-hole 9 and the leg-holes 11 are respectively provided along edges thereof with a plurality of elastic members 12, 13 secured thereto in a stretched state. The absorbing component 3 extends on the inner surface 2a of the covering component 2 over the crotch region 8 into the front waist region 6 and the rear waist region 7. The absorbing component 3 is folded toward a longitudinal center line A—A (See FIG. 4 also) bisecting a width of the diaper 1 and extending in the height direction, i.e., inwardly in a transverse dimension of the diaper 1 so that a transverse direction of the diaper 1 may be reduced in the crotch region 8.

Figure 4:
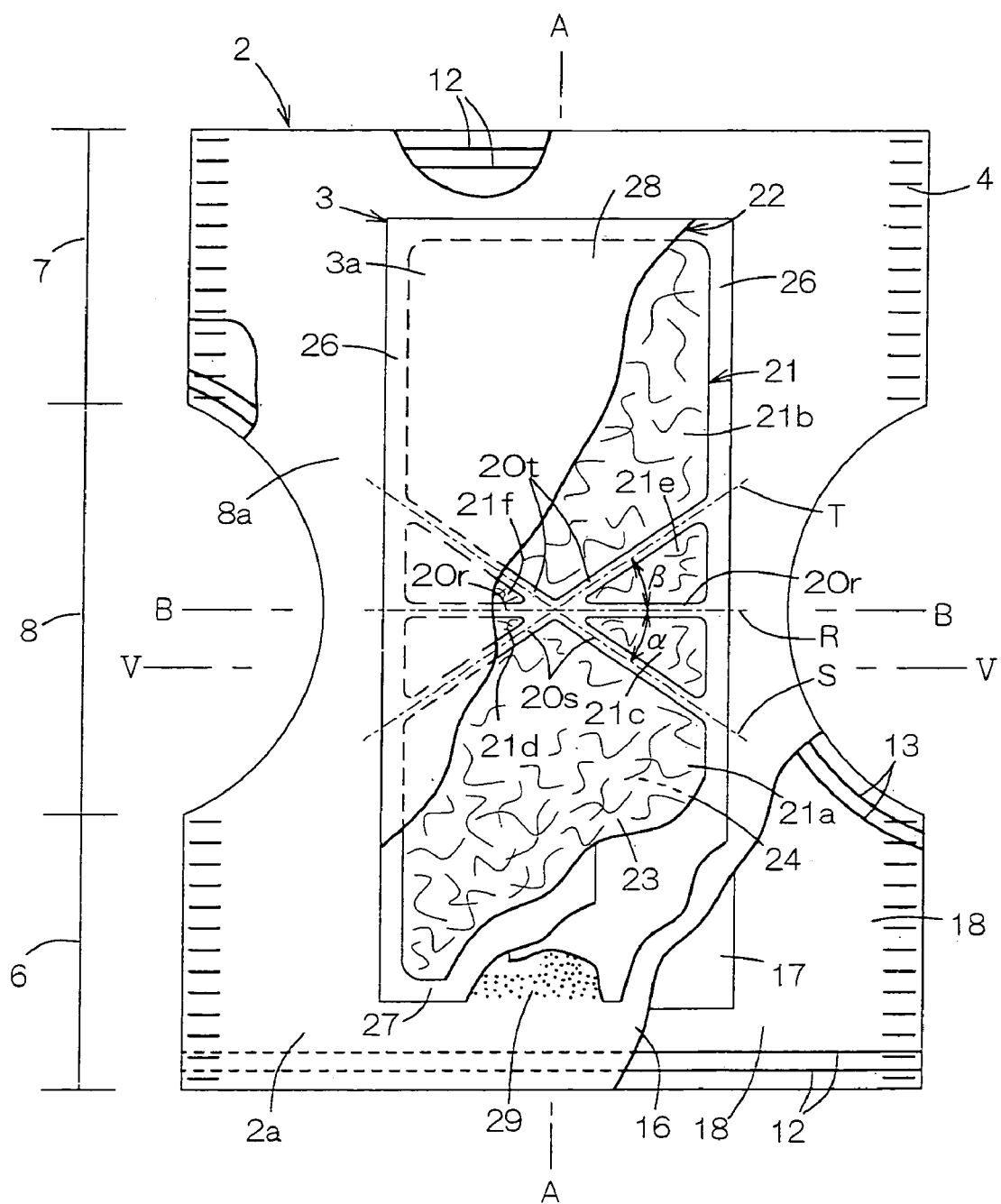
FIG. 4 is a developed plan view showing the diaper of FIG. 2.
Figure 5:
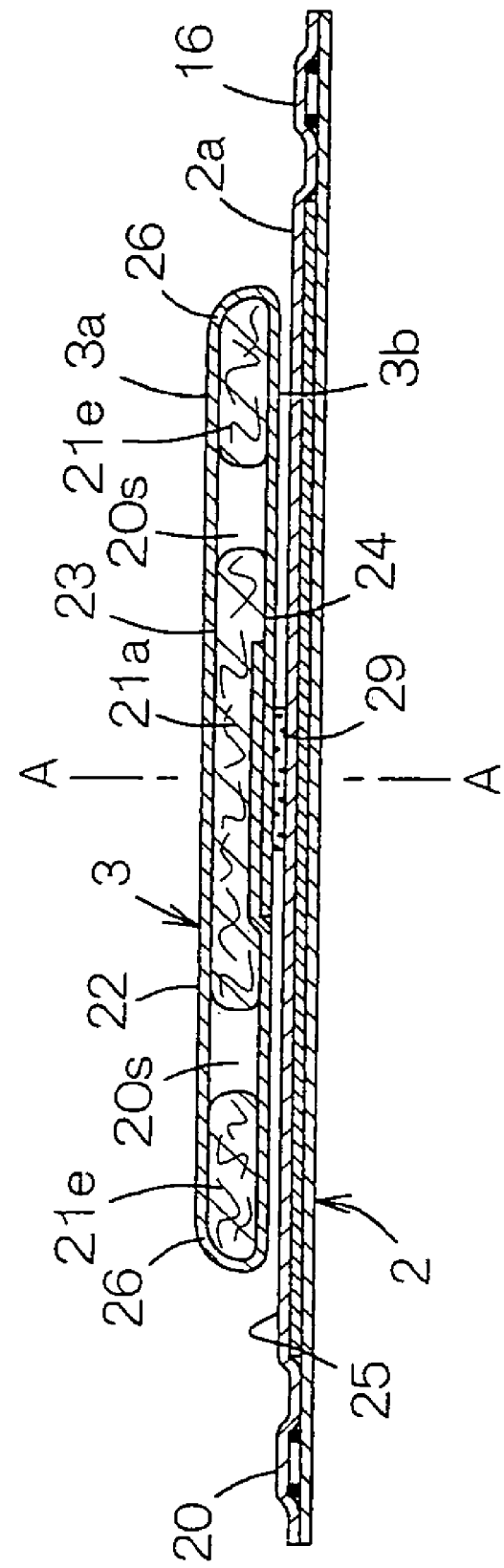
FIG. 5 is sectional view taken along a line V—V in FIG. 4.

FIG. 4 is a partially cutaway plan view showing the diaper 1 of FIGS. 1, 2 with its front and rear waist regions 6, 7 having been peeled off from each other along securing zones 4 and developed in opposite directions indicated by arrows P, Q and FIG. 5 is a sectional view taken along a line V—V in the plan view. As shown in FIG. 4, a transverse center line B—B bisecting a vertical length of the diaper 1 extends in a direction crossing the longitudinal center line A—A. In the developed state as shown in FIG. 4, the diaper 1 is substantially symmetric about the longitudinal center line A—A and may be folded back along the transverse center line B—B to obtain the diaper 1 in the state as shown in FIG. 1.

Referring to FIGS. 4 and 5, the covering component 2 comprises a hourglass-shaped inner sheet 16 made of breathable nonwoven fabric, more preferably, hydrophobic breathable nonwoven fabric, an intermediate sheet 17 made of liquid-impervious plastic film, more preferably, breathable and liquid-impervious plastic film having a rectangular shape substantially identical to the planar configuration of the absorbing component 3 or having a size larger than the planar configuration of the absorbing component 3 and an outer sheet 18 made of breathable nonwoven fabric and being identical to the inner sheet 16 in shape as well as in size. These sheets 16, 17, 18 may be laminated and intermittently joined together using appropriate adhesives or welding techniques to form the covering component 2. The waist-surrounding elastic members 12 and the leg-surrounding elastic members 13 are interposed between the inner sheet 16 and the outer sheet 18 and secured to at least one of these sheets 16, 18 by means of adhesives (not shown).

Referring to FIG. 4, the absorbing component 3 has a rectangular shape which is relatively long in a vertical direction as viewed in FIG. 4. This rectangular absorbent component 3 is contoured by transversely opposite side edges 26 extending in parallel to the longitudinal center line A—A and front and rear ends 27, 28 extending in the transverse direction crossing the transversely opposite side edges 26. The absorbing component 3 comprises a core 21 and a cover sheet 22 bonded to the inner surface 2a of the covering component 2 by means of hot melt adhesives 29 along the longitudinal center line A—A and the front and rear ends 27, 28. The cover sheet 22 is made of liquid-pervious nonwoven fabric or perforated plastic film and the core 21 is formed by absorbent material such as fluff pulp or super-absorbent polymer particles compressed under appropriate pressure and, if desired, wrapping the absorbent material having been compressed in this manner with a tissue paper or a nonwoven fabric made of hydrophilically modified thermoplastic synthetic fibers. While the core 21 is illustrated to define a rectangle in entirety, it should be understood that the core 21 has grooves 20r, 20s, 20t (See FIG. 5 also) extending along a chain line R respectively extending in coincidence with the transverse center line B—B, a chain line S extending so as to describe a V-shape from a central zone of the core 21 defined by the intersection of the longitudinal center line A—A and the transverse center line B—B toward the front waist region 6 to the transversely opposite side edges 26 and a chain line T extending so as to describe a V-shape from the central zone of the core 21 defined by the intersection of the longitudinal center line A—A and the transverse center line B—B toward the rear waist region 7 to the transversely opposite side edges 26. These grooves 20r, 20s, 20t divide the core 21 into core elements 21a, 21b, 21c, 21d, 21e, 21f. α designates an angle included between the groove 20r and the groove 20s and β designates an angle included between the groove 20r and the groove 20t. These angles α and β are illustrated to be equal to each other. In the crotch region 8, the width of the absorbing component 3 is smaller than the width of the crotch region 8 and, in FIGS. 1, 2 and 3, side edge portions 8a of the crotch region 8 defining the respective leg-holes 11 lie on the outer surface of the absorbing component 3 and extend outwardly in the transverse direction of the diaper 1 beyond the opposite side edges 26 of the absorbing component 3 so as to form leg-surrounding flaps fully surrounding the respective leg-holes 11. The respective core elements 21a–21f may be intermittently bonded to the cover sheet 22 or the tissue paper wrapping them by means of hot melt adhesives to retain a given relative position of these core elements.

From the state as shown in FIG. 4, the diaper 1 having the absorbing component 3 formed in such manner is folded back along the transverse center line B—B and then the front and rear waist regions 6, 7 are joined together at the securing zones 4 to obtain the diaper 1 in the state as shown in FIGS. 1, 2 and 3. Thereupon, both side portions of the absorbing component 3 with respect to the longitudinal center line A—A are folded toward the longitudinal center line A—A as shown in FIG. 2. More specifically, the absorbing component 3 is folded along the groove 20r so that the outer surface 24 of the core elements 21c is opposed to the outer surface 24 of the 21e (See FIG. 5) while the outer surface 24 of the core element 21d and the outer surface 24 is opposed to the outer surface 24 of the core element 21f. At the same time, the absorbing component 3 is folded along the groove 20s and the groove 20t so that the inner surface 23 of the core element 21a is opposed to the inner surfaces 23 of the respective core elements 21c, 21d while the inner surface 23 of the core element 21b is opposed to the inner surfaces 23 of the respective core elements 21e, 21f (See FIG. 4). In the absorbing component 3, the grooves 20r, 20s, 20t are free from the core 21 or contain the core 21 at an extremely low density, so the absorbing component 3 has its stiffness lower in these grooves 20r, 20s, 20t than in the other region. In addition, the portion of the absorbing component 3 lying along the longitudinal center line A—A are bonded to the inner surface 2a of the covering component 2 but the opposite side edges 26 as well as the vicinity of these side edges 26 are not bonded to the inner surface 2a of the covering component 2 as will be apparent from FIGS. 2–5. This arrangement facilitates the absorbing component 3 to be folded along the grooves 20r, 20s, 20t as shown in FIG. 2.

In the pull-on disposable diaper 1 arranged as has been described in reference to FIGS. 1 and 2, the opposite side edges 26, 26 of the absorbing component 3 folded so that the width of the absorbing component 3 may be reduced in the crotch region 8 and those opposite side edges 26, 26 may extend upwardly advantageously come in close contact with the wearer's crotch. In addition, these opposite side edges 26, 26 extending upwardly lie adjacent to the wearer's genital organ and therefore discharged urine is rapidly absorbed without spreading in the transverse direction. A space defined between these opposite side edges 26, 26 forms an inner pocket 30a (See FIG. 2) hollowing downward to a sufficient depth to be spaced from the wearer's body and it is not likely that the inner surface 3a of the absorbent component 3 wetted with the discharge urine might come in contact with the wearer's body over a large area and create an uncomfortable damp feeling against the wearer. Even if the discharged urine is not properly received in this pocket 30a but flows beyond the opposite side edges 26 into spaces defined outside this inner pocket 30a, transversely opposite side edge portions 8a of the crotch region 8 which lie outside the opposite side edges 26 and tightly enclose the wearer's legs in the form of flaps function as barriers against leakage of the bodily discharges from the diaper 1. Furthermore, the outer surface 24 of the core 21 is covered with the liquid-pervious cover sheet 22 at least in the vicinity of the opposite side edges 26 as seen in FIGS. 2, 3 and 4 and therefore a partial amount of bodily discharges staying in outer pockets 30b defined by the portions of the absorbing component 3 extending upwardly and the opposite side edge portions 8a of the crotch region 8 after having flown beyond the respective side edges 26 can be absorbed also by the outer surface 24 of the core 21. In this way, the preventive effect of the diaper 1 against leakage of bodily discharges can be further improved. It should be understood that it is also possible to cover at least a part of the outer surface 24 of the core 21 in the transverse direction, for example, the middle portion thereof in the transverse direction with a liquid-impervious sheet.

To put the diaper 1 on an infant's body, his or her mother may guide infant's legs through the waist-hole 9 opened as widely as possible with the mother's hands put against the inner side of the waist-hole 9 into the respective leg-holes 11. With this diaper 1, the absorbing component 3 provided separately of the covering component 2 in the crotch region 8 remote from the waist-hole 9 is not affected by deformation of the diaper 1 occurring as the waist-hole 9 is opened in this manner. Furthermore, even when the side edge portions 8a of the crotch region 8 move as the leg-holes 11 are opened, the absorbing component 3 is substantially not responsive to such a movement because the side edges 26 of the absorbing component 3 are not bonded to the side edge portions 8a of the crotch region 8. Therefore, the absorbing component 3 folded so that its width may be appropriately reduced is well protected from getting out of its initial shape and the side edges 26 extending upwardly reliably come in close contact with the crotch of the infant. In this diaper 1, the absorbing component 3 folded so that its width may be reduced reliably provides its expected effect once the diaper 1 has been put on the infant's body. Depending on the thickness of the core 21, it is possible that the absorbing component 3 is folded as shown in FIG. 2 not along the groove 20r but along the grooves 20s, 20t. It is also possible to locally compress or to compress under heating the zones of the absorbing component 3 extending along the chain lines R, S, T or the chain lines S, T using embossing rolls or the like so that the absorbing component 3 may have stiffness higher in these zones than in the other zone and the absorbing component 3 may be folded along these high stiffness zones serving as the folding guides.

Figure 6:
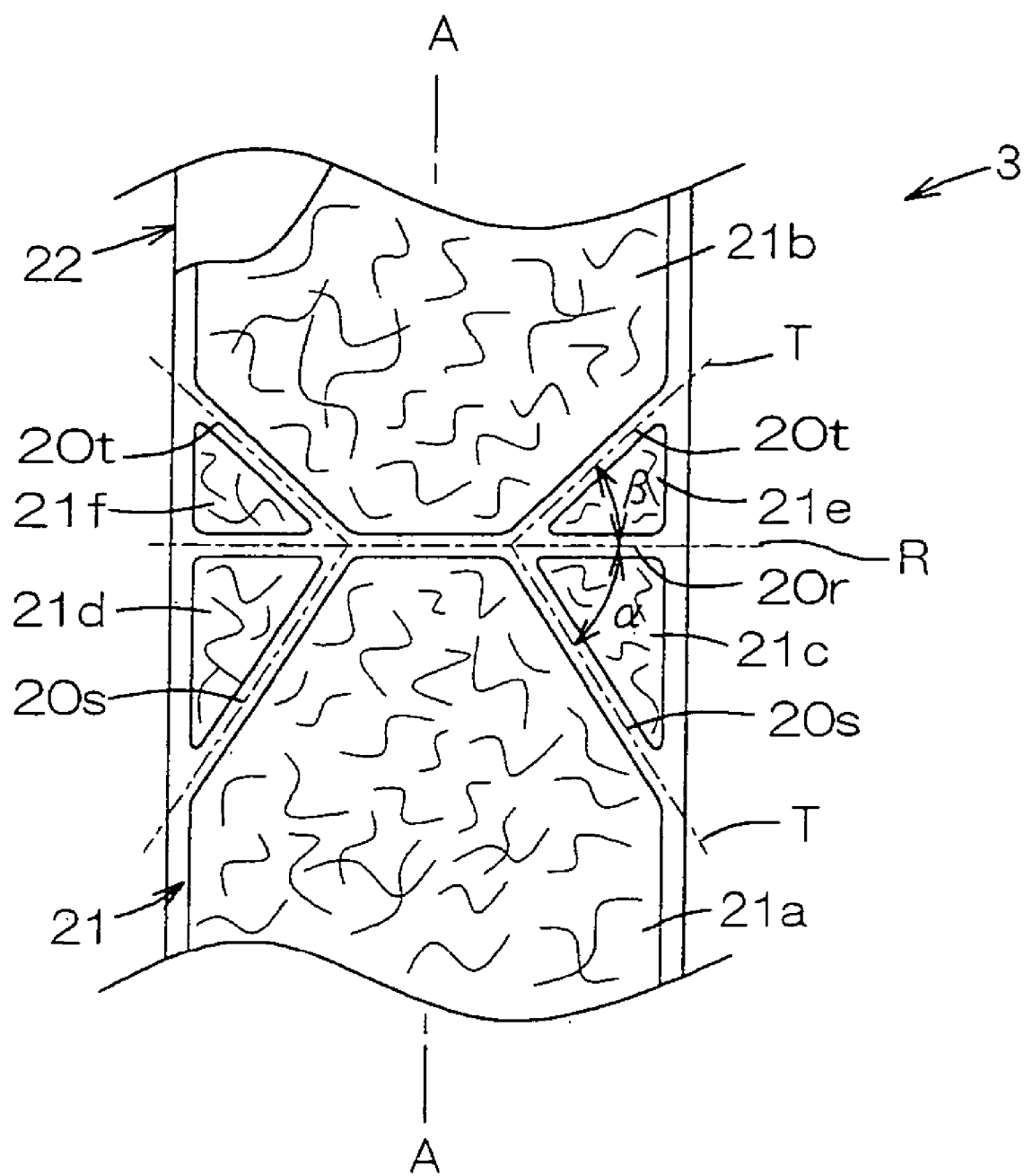
FIG. 6 is a diagram illustrating an important part of an absorbing component different from one of FIG. 4.

FIG. 6 is a diagram illustrating an important part of an absorbing component 3 arranged in a manner different from that shown in FIG. 4. In the core 21 of this absorbing component 3, the left and right grooves 20s, 20s extend in a direction intersecting the longitudinal center line A—A with spacing from each other in the transverse direction of the core 21 so as to describe a V-shape. The left and right grooves 20t, 20t are spaced from each other in the similar manner. The angle α included between the grooves 20r and the groove 20s is larger than the angle β included between the groove 20r and the groove 20t. It is possible to differentiate the angles α and β and to select a distance between the left and right grooves 20s, 20s; 20t, 20t.

Figure 7:
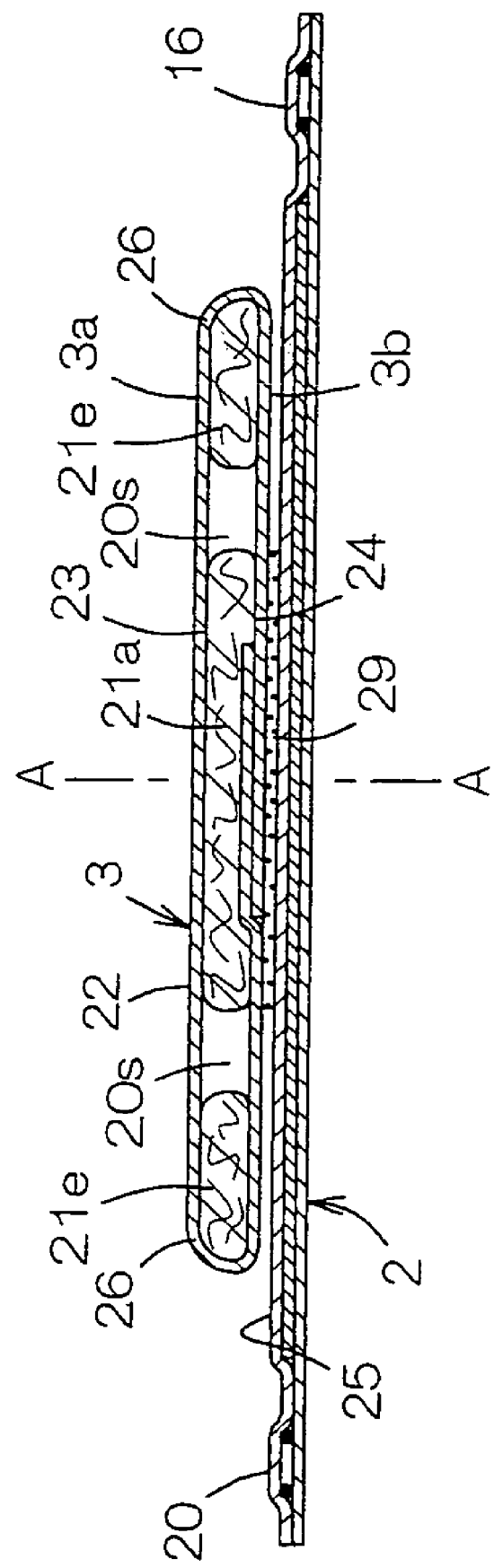
FIG. 7 is a sectional view similar to FIG. 5, showing one preferred embodiment of this invention.

FIG. 7 is a sectional view similar to FIG. 5, showing one preferred embodiment of this invention. Of the cover sheet 22 of the absorbing component 3 in this diaper 1, the region covering the core elements 21a, 21b is bonded to an inner sheet 25 by means of the hot melt adhesives 29 and the region covering the other core elements 21c–21f and the zones corresponding to the chain lines R, S, T is not bonded to the inner sheet 25.

Figure 8:
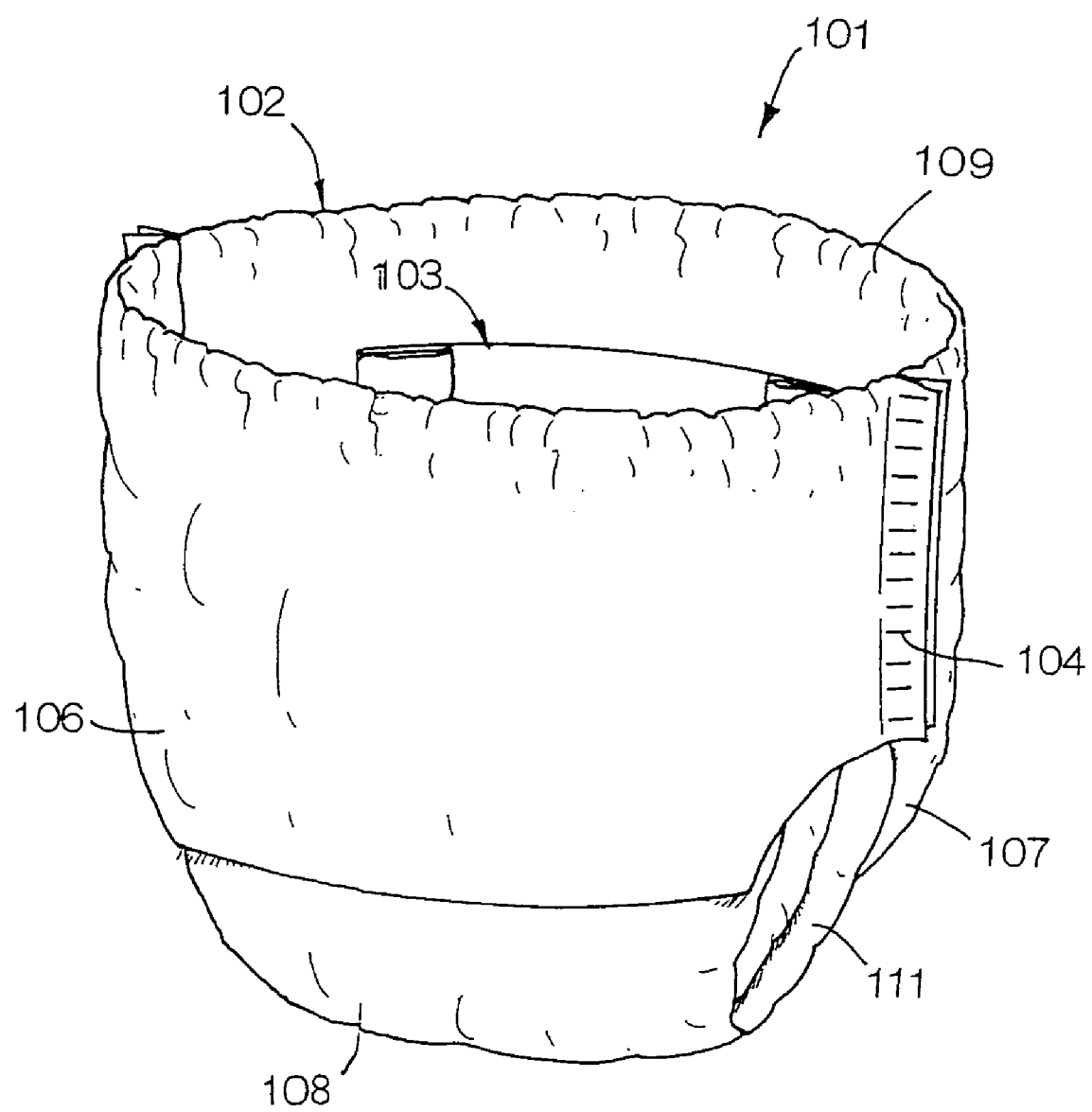
FIG. 8 is a perspective view showing another preferred embodiment of this invention.
Figure 9:
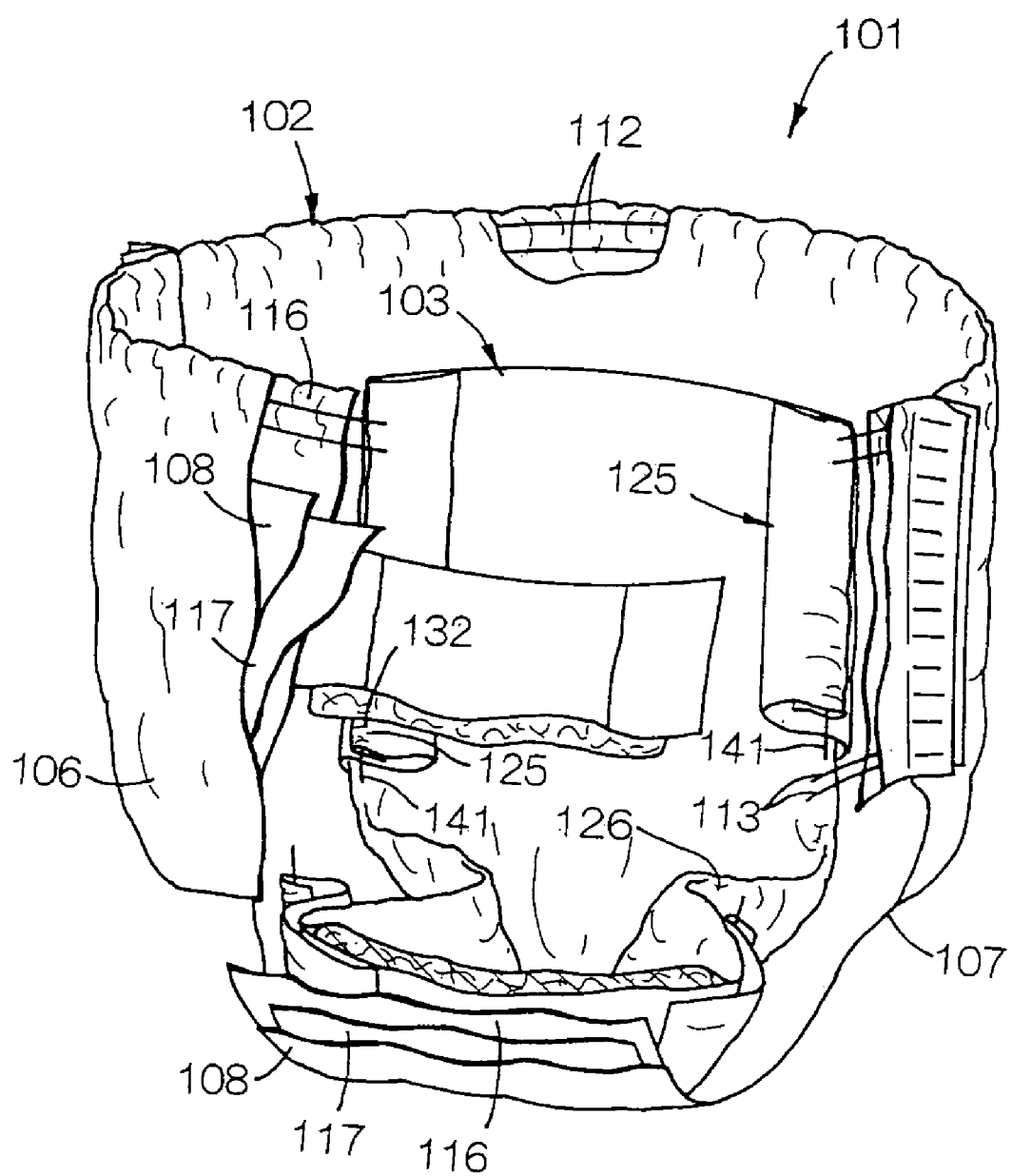
FIG. 9 is a partially cutaway perspective view showing the diaper of FIG. 8.
Figure 10:
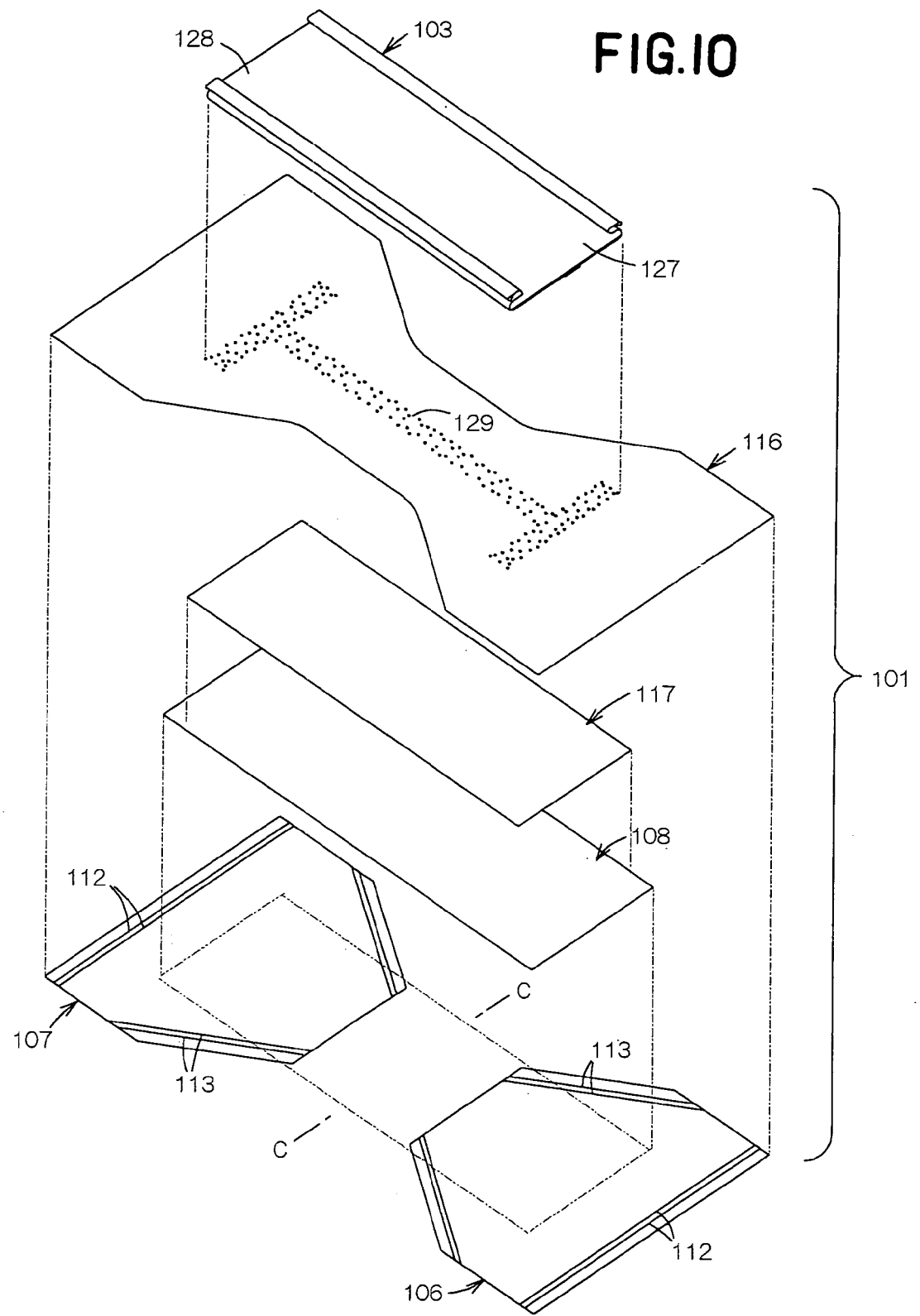
FIG. 10 is a exploded perspective view showing the diaper of FIG. 8.

FIG. 8 is a perspective view showing a pull-on disposable diaper 101 as another preferred embodiment of this invention, FIG. 9 is a partially cutaway perspective view showing this diaper and FIG. 10 is an exploded perspective view showing this diaper. This diaper 101 basically comprises a covering component 102 adapted to cover the wearer's body and an absorbing component 103 adapted to contain bodily discharges. The covering component 102 comprises a hexagonal front sheet 106 defining the front waist region and a part of the crotch region, a hexagonal rear sheet 107 defining the rear waist region and a part of the crotch region and a rectangular center sheet 108 defining a part of the crotch region. The center sheet 108 has longitudinally opposite ends bonded to the inner surfaces (the upper surfaces as viewed in FIG. 10) of the front and rear sheets 106, 107 by means of hot melt adhesives (not shown) and thereby connects the front and rear sheets 106, 107. An intermediate sheet 117 made of rectangular water-proof film is placed upon the inner surface of the center sheet 108 and an hourglass-shaped inner sheet 116 is placed upon the inner surface of the intermediate sheet 117. In the case of the illustrated embodiment, the intermediate sheet 117 is identical in shape as well as in size to the center sheet 108 or slightly smaller than the center sheet 108. The inner sheet 116 is substantially identical in shape as well as in size to the hourglass-shape defined by the front, rear and center sheets 106, 107, 108 connected one to another. These sheets 106, 107, 108, 117 and 116 are intermittently bonded together on each pair of adjacent surfaces placed one upon another. Between the front sheet 106 and the inner sheet 116 as well as between the rear sheet 107 and the inner sheet 116, waist-surrounding elastic members 112 and leg-surrounding elastic members 113 are secured to these sheets in a stretched state. A primary function of the center sheet 108 is to connect the front and rear sheets 106, 107 to each other and therefore it is possible to dimension this center sheet 108 to be smaller than the intermediate sheet 117 so long as the primary function is achieved.

A rectangular absorbing component 103 having its longitudinal direction corresponding to the longitudinal direction of the center sheet 108 is bonded to the inner surface of the inner sheet 116. The absorbing component 103 has its front and rear ends 127, 128 and its transversely middle zone extending between these ends 127, 128 bonded to the inner sheet 116. These sheets 106, 107, 108, 117, 116 and the absorbing component 103 placed upon and bonded to one to another as shown in FIG. 10 may be folded back along a line C—C with the absorbing component 103 inside thereof and these front, rear and inner sheets 106, 107, 116 may be bonded together at zones 104 arranged intermittently along the side edges thereof to obtain the pull-on disposable diaper 101. The sheets 106, 107, 108, 117 and 116 as shown in FIG. 10 cooperate to form the pants-like covering component 102 corresponding to the covering component 2 in FIG. 1. The line C—C in FIG. 10 is a transverse center line corresponding to the transverse center line B—B in FIG. 2 and bisects a length of the flatly developed diaper 101. The zones 104 correspond to the zones 4 in FIG. 1. Like the diaper 1, the covering component 102 has a waist-hole 109 and a pair of leg-holes 111. The absorbing component 103 is folded inward of the diaper 101, like the absorbing component 3 in FIG. 3, so that the width of the absorbing component 103 may be reduced in the crotch region 108.

Figure 11:
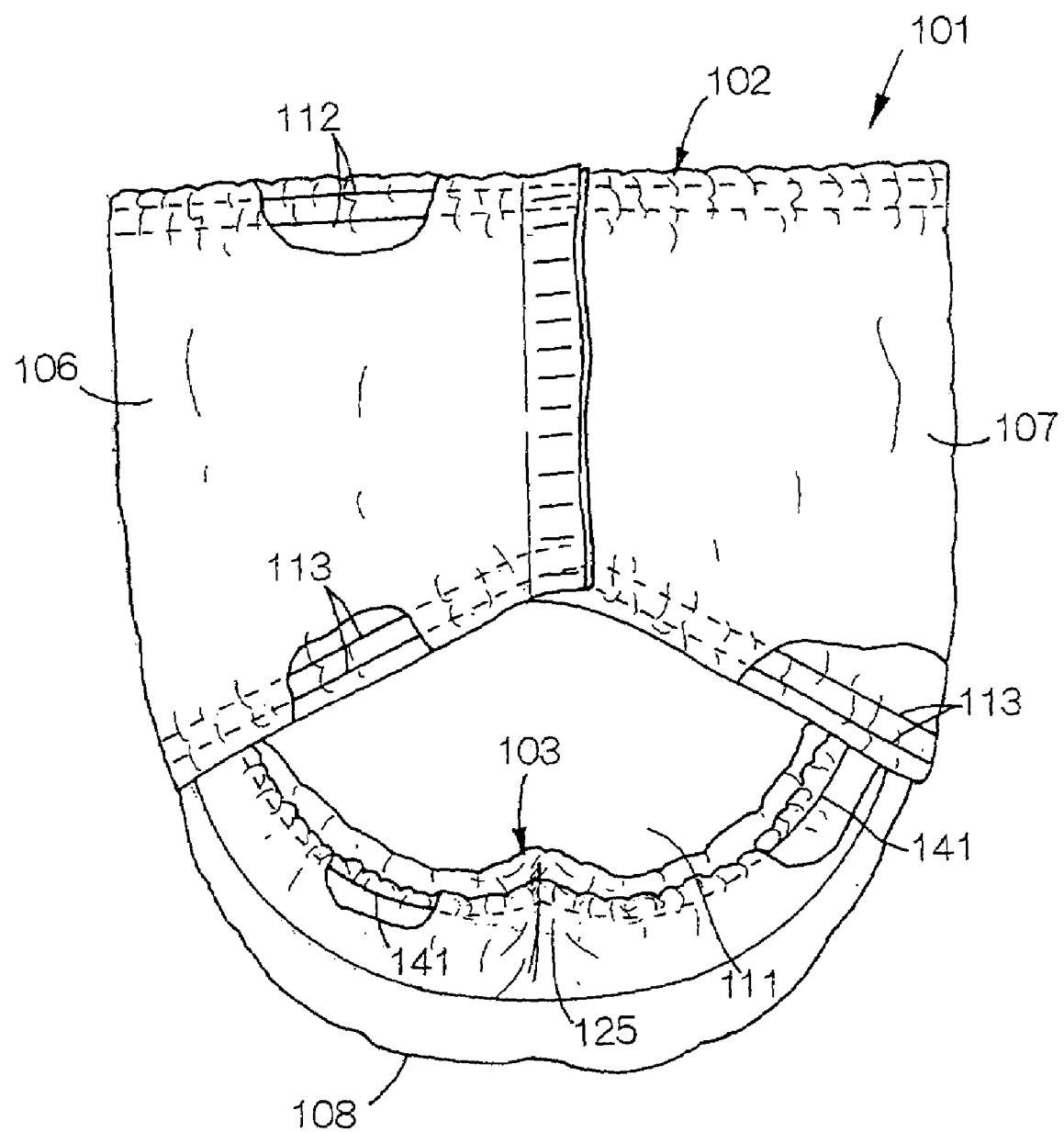
FIG. 11 is a partially cutaway side view showing the diaper of FIG. 8.

FIG. 11 is a partially cutaway side view showing the diaper 101 of FIG. 8. In FIG. 11, the elastic members exposed in the part cutaway are indicated by solid lines and the elastic members which are contiguous to these solid lines are indicated by dashed lines. As shown, the leg-surrounding elastic members 113 extend along an approximately upper half peripheral edge of the respective leg-holes 111.

Figure 12:
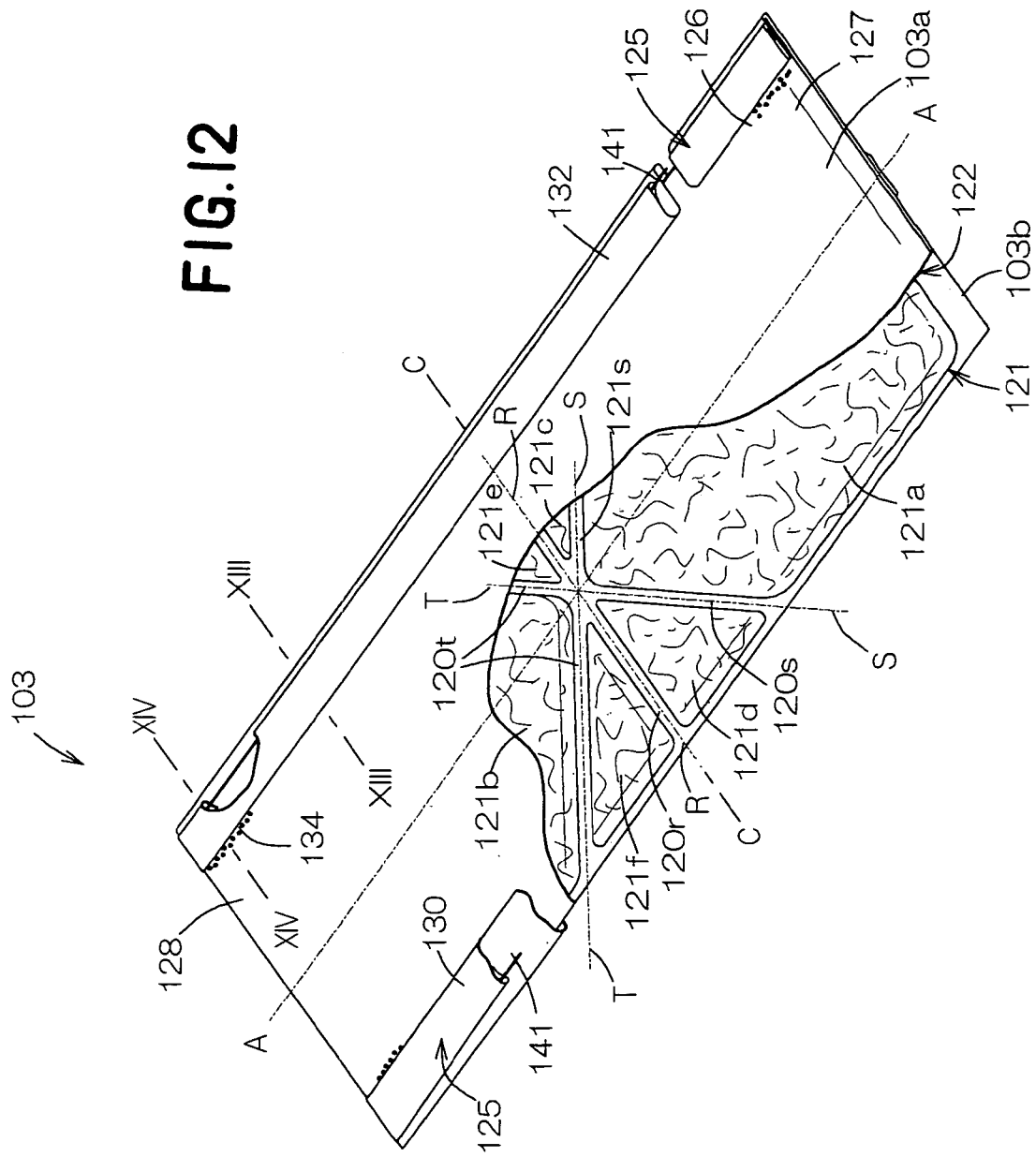
FIG. 12 is a partially cutaway perspective view showing the absorbing component of FIG. 10.

FIG. 12 is a partially cutaway perspective view showing the absorbing component 103 of FIG. 10. The absorbing component 103 comprises an absorbent core 121, a cover sheet 122 and flaps 125. The core 121 and the cover sheet 122 are identical to the core 21 and the cover sheet 22 in FIG. 4, respectively. Specifically, the core 121 is formed with grooves 120r, 120s, 120t along a straight chain line R coinciding with the center line C—C and substantially V-shaped chain lines S and T and divided by these grooves into core elements 121a, 121b, 121c, 121d, 121e and 121f. These chain lines R, S, T, grooves 120r, 120s, 120t and core elements 121a–121f correspond to the chain lines R, S, T, the grooves 20r, 20s, 20t and the core elements 21a–21f in FIG. 4. The manner in which the absorbing component 103 are folded inward of the diaper 101 so as to have its width reduced in the crotch region 108 is also similar to the manner shown in FIG. 4.

Figure 13:
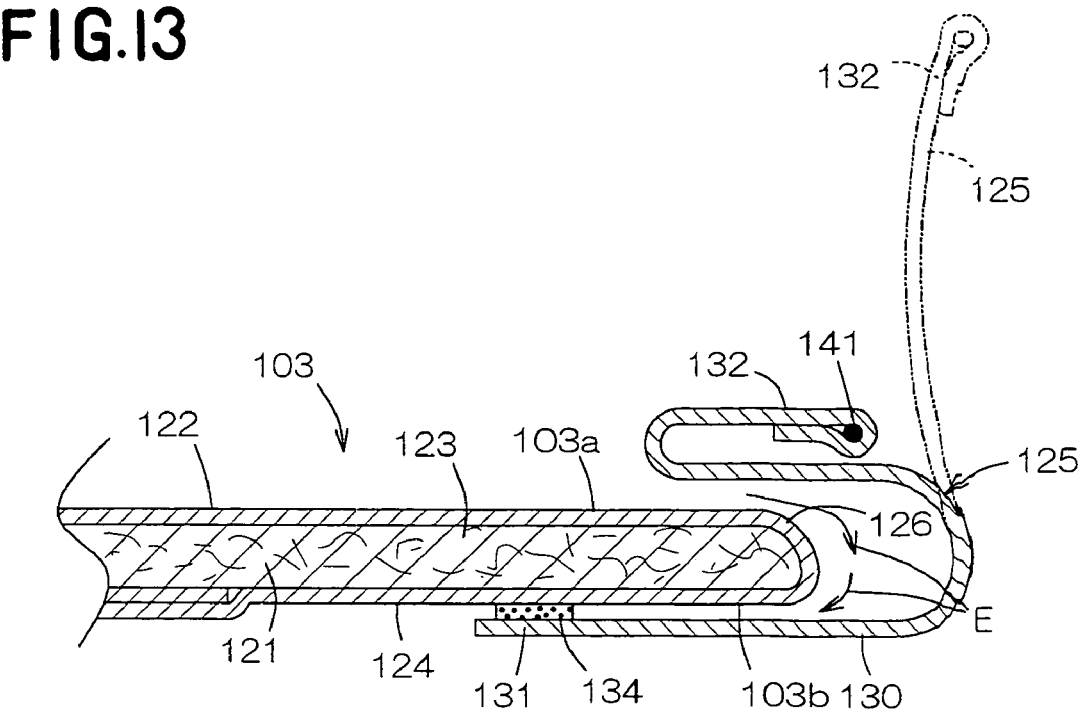
FIG. 13 is a sectional view taken along a line XIII—XIII in FIG. 12.
Figure 14:
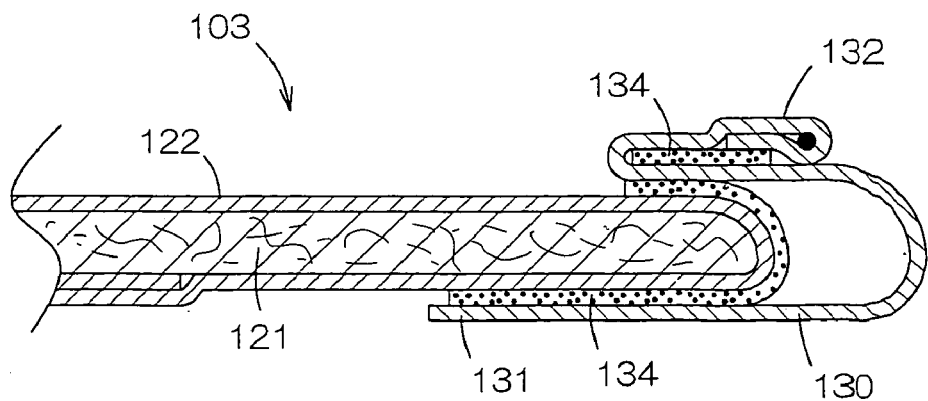
FIG. 14 is a sectional view taken along a line XIV—XIV in FIG. 12.
Figure 15:
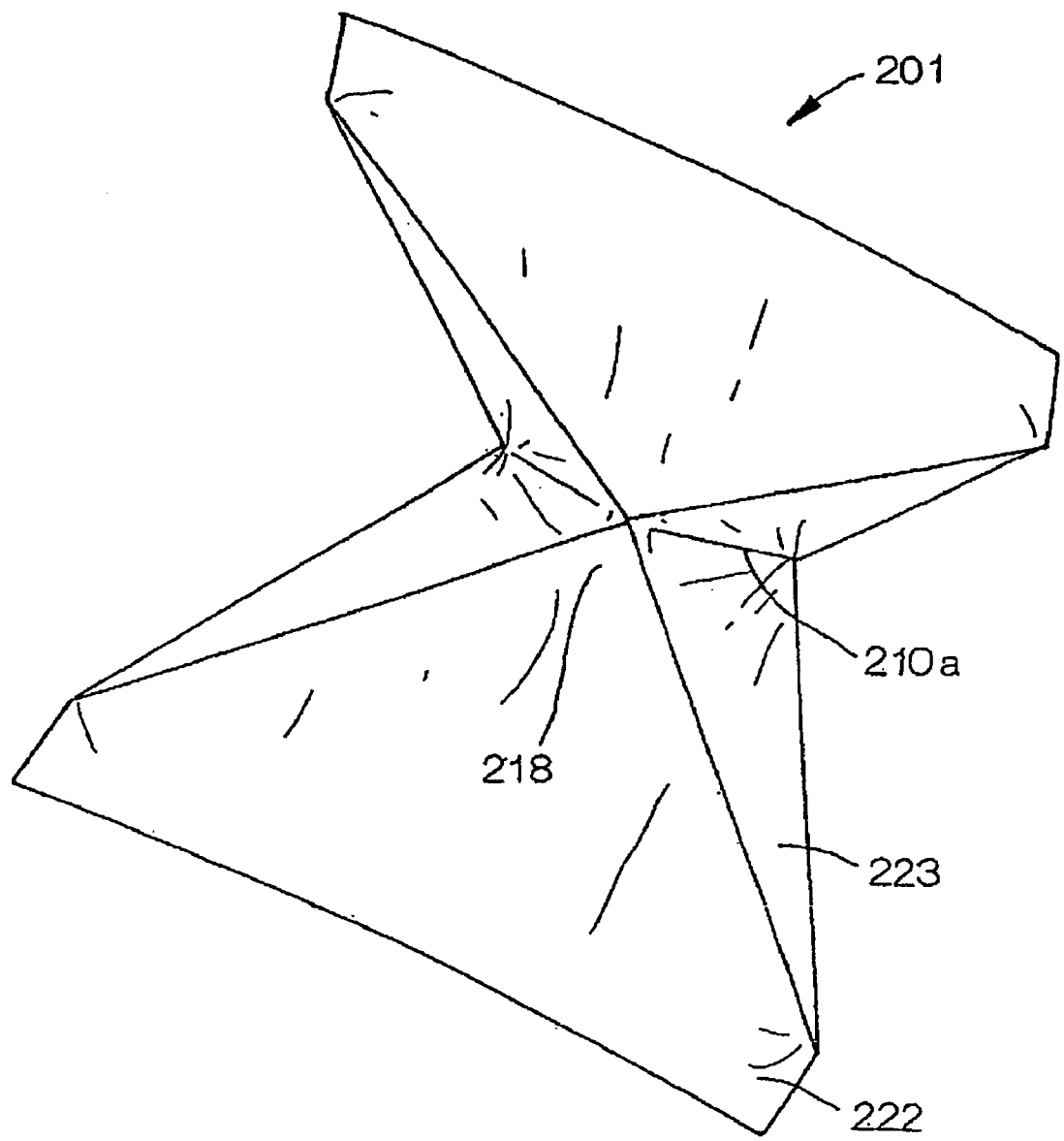
FIG. 15 is a perspective view showing an example of the conventional diaper.

FIG. 13 is a sectional view taken along a line XIII—XIII in FIG. 12 and FIG. 14 is a sectional view taken along a line XIV—XIV in FIG. 12. The flaps 125 are formed by leak-barrier sheets 130 extending along transversely opposite side edges 126 of the absorbing component 103. Each of these leak-barrier sheets 130 is made of a hydrophobic, preferably liquid-impervious, more preferably breathable and liquid-impervious nonwoven fabric or a plastic film or a laminated sheet consisting of these nonwoven fabrics and films. The leak-barrier sheet 130 is folded in a Z-shape or an inverted Z-shape in its transverse direction and fixed along one side edge 131 of its transversely opposite side edges 131, 132 to the cover sheet 122 on the outer surface 103b of the absorbing component 103 by means of an adhesive 134. The other side edge 132 lies above the inner surface 103a of the absorbing component 103 so that the side edge 132 may be deformed in a vertical direction as well as in a horizontal direction as viewed in FIG. 13. The outermost rounded fold of the side edge 132 wraps an elastic member 141 extending in the longitudinal direction of the absorbing component 103 and fixed thereto in a stretched state. Between the transversely opposite side edges 131, 132, the leak-barrier sheet 130 extends outwardly from the side edge 131 toward the side edge 132 beyond the side edge 126 of the absorbing component 103, then is folded back toward the inner surface 103a and folded again outward of the absorbing component 103. It should be understood that, in the vicinity of longitudinally opposite ends 127, 128 of the absorbing component 103, each of the leak-barrier sheets 130 folded in a Z-shape or an inverted Z-shape is maintained in such a folded state by the adhesive 134 as shown in FIG. 14. In other words, the leak-barrier sheet 130 is partially bonded to itself and the cover sheet 122 and the leak-barrier sheet 130 are also partially bonded together by means of the adhesive 134.

With the diaper 101 put on the wearer's body and the absorbing component 103 curved in its longitudinal direction, the flaps 125 each formed by the leak-barrier sheet 130 are biased by a contractile force of the elastic members 141 to rise above the inner surface 103 of the absorbing component 103 immediately outside the respective outermost rounded folds 126 and between the longitudinally opposite ends 127, 128 of the absorbing component 103. The flap 125 rising in this manner will be seen in a state cutaway partially in FIG. 9. The flap 125 in its rising state is indicated by solid lines in FIG. 11 and by imaginary lines in FIG. 13. Such a unique behavior of the flap 125 ensures that the side edge 132 of the leak-barrier sheet 130 is tightly placed around the wearer's thigh under the effect of the elastic member 141. The flaps 125 tightly placed around the wearer's thigh serve as barriers against any amount of bodily discharges having flown sideways beyond the side edges 126 of the absorbing component 103 and these barriers eliminate an anxiety that any amount of bodily discharges might leak out from the diaper 101. This preventive effect is particularly significant in the portion of the absorbing component 103 folded so that the width of the absorbing component 103 may be reduced in the crotch region 108 of the diaper 101 as shown in FIG. 9. The elastic member 141 of the flap 125 describes a U-shape and goes approximately half around the wearer's thigh and portions defining branches of this U-shape extending upwardly indirectly overlap the leg-surrounding elastic members 113 in the front and rear sheets 106, 107 (See FIG. 11). These elastic members 113, 114 ensure the leg-holes of the diaper 101 to be maintained in close contact with the wearer's legs over full circumferences. While the elastic member 141 associated with each of the flaps 125 is illustrated as a single elastic member, this may be replaced by a plurality of elastic members.

In the diaper 101 of FIG. 8, it is also possible to arrange the leak-barrier sheet 130 so that, on the outer surface 103b of the absorbing component 103, particularly in the vicinity of the side edge 126, the leak-barrier sheet 130 can be separated from the cover sheet 122 downward as viewed in FIG. 13. With this alternative arrangement, an amount of bodily discharges having flown beyond the side edge 126 in a direction indicated by an arrow E into a space defined between the outer surface 103b of the absorbing component 103 and the associated leak-barrier sheet 130 is absorbed by the core 121 through the cover sheet 122 on the outer surface 103b of the absorbing component 103.

In this diaper 101 also, the side edges 126 of the absorbing component 103 folded in the crotch region 108 so as to have its width reduced can be fitly placed against the wearer's body while the inner pocket of the absorbing component 103 defined between the transversely opposite side edges 126, 126 does not come in contact with the wearer's body. The side edges 126 folded in this manner do not get out of the folded postures even when the waist-hole 109 (See FIG. 8) is opened as widely as possible.

The pull-on disposable diaper according to this invention has advantageous effects that the absorbing component extending over the crotch region into the front and rear waist regions is folded so that the absorbing component may have its width reduced in the crotch region and be in contact with the wearer's body only along the transversely opposite side edges thereof. With this unique arrangement, the wearer is free from a damp feeling even after the absorbing component has absorbed bodily discharges. Combination of the absorbing component with the pull-on diaper ensures that the portion of the absorbing component folded so as to have its width reduced in the crotch region does not get out of the folded postures in the course of putting the diaper on the wearer's body. According to the embodiment in which the absorbing component is provided on its outer surface with the flaps extending outwardly from the transversely opposite side edges of the absorbing component, any amount of bodily discharges has flown outwardly beyond the folded zone of the absorbing component can not leak from the diaper.

What is claimed is:

1. A pull-on disposable diaper having a height direction and a transverse direction being orthogonal to said height direction, said diaper being generally symmetric about a center line bisecting said diaper in said transverse direction, said diaper comprising a pants-like covering component having an inner surface facing a wearer's body and an outer surface facing a wearer's garment, said covering component being composed of a front waist region, a rear waist region and a crotch region adapted to cover a wearer's front region, a wearer's rear region and a wearer's crotch region, respectively, said covering component having a waist-hole and a pair of leg-holes, and being provided with an absorbing component which is separate from the pants-like covering component and disposed on said inner surface of said pants-like covering component so as to extend over said crotch region into said front and rear waist regions, said pull-on disposable diaper further comprising: said absorbing component comprising a liquid-absorbent core and a liquid-pervious cover sheet, said core having a generally rectangular shape and having an inner surface and an outer surface, said cover sheet covering at least said inner surface of said inner and outer surfaces of said core, said absorbing component being formed in said crotch region with a first folding guide extending from a middle zone between transversely opposite side edges which extend, in turn, parallel to each other in said height direction to respective said side edges so as to veer toward said front waist region, a second folding guide extending to respective said side edges so as to veer toward said rear waist region and a third folding guide extending in a transverse direction between said first and second folding guides, and said absorbing component being folded on both sides of said center line along said third folding guide so that said core has its outer surface sections facing to each other and along said first and second folding guides so that said core has its inner surface sections facing to each other, and wherein said crotch region is provided on said outer surface of said absorbing component with flaps extending outward of said absorbing component in said transverse direction and defining peripheral edges of respective said leg-holes, said flaps being elastically stretchable in a circumferential direction of said leg-holes, said outer surface of said absorbing component being separated from said flaps at least along said side edges and in vicinities of said side edges and zones separated from said flaps are covered with said cover sheet.

2. The disposable diaper according to claim 1, wherein at least said first and second folding guides of said first-third folding guides serve as V-shaped folding guides having a relatively low stiffness which are formed in said absorbing component.

3. The disposable diaper according to claim 1, wherein at least said first and second folding guides of said first-third folding guides serve as V-shaped folding guides having a relatively high stiffness which are formed in said body fluid absorbent component.

4. The disposable diaper according to claim 1, wherein said crotch region includes a liquid-impervious sheet, said cover sheet being folded back so as to wrap not only said inner surface of said core but also said outer surface of said core in vicinities of said side edges, and said core being capable, in vicinities of said side edges, of absorbing bodily discharges present between said cover sheet and said liquid-impervious sheet from said outer surface through said cover sheet.

5. The disposable diaper according to claim 1, wherein said outer surface of said core is covered in a transversely middle zone with a liquid-impervious sheet.

6. The disposable diaper according to claim 4, wherein said diaper has at least said cover sheet on a side of its outer surface of said core, a breathable nonwoven fabric sheet on an outer surface of said cover sheet, and a plastic film on an outer surface of said nonwoven fabric sheet as said liquid-impervious sheet.

* * * * *